United States Patent
Dalvi

(10) Patent No.: US 9,891,079 B2
(45) Date of Patent: Feb. 13, 2018

(54) PULSER WITH DOUBLE-BEARING POSITION ENCODER FOR NON-INVASIVE PHYSIOLOGICAL MONITORING

(71) Applicant: Masimo Corporation, Irvine, CA (US)

(72) Inventor: Cristiano Dalvi, Irvine, CA (US)

(73) Assignee: Masimo Corporation, Irvine, CA (US)

(*) Notice: Subject to any disclaimer, the term of this patent is extended or adjusted under 35 U.S.C. 154(b) by 314 days.

(21) Appl. No.: 14/334,662

(22) Filed: Jul. 17, 2014

(65) Prior Publication Data

US 2015/0045637 A1 Feb. 12, 2015

Related U.S. Application Data

(60) Provisional application No. 61/847,307, filed on Jul. 17, 2013.

(51) Int. Cl.
*G01D 5/347* (2006.01)
*G01D 11/02* (2006.01)
*A61B 5/1455* (2006.01)

(52) U.S. Cl.
CPC ........ *G01D 5/34738* (2013.01); *A61B 5/1455* (2013.01); *G01D 11/02* (2013.01)

(58) Field of Classification Search
CPC ........... G01D 5/34738; G01D 5/34707; G01D 5/347; G01D 5/3473; G01D 5/34715; G01D 5/34723; G01D 11/02; A61B 5/1455; A61B 5/14552
USPC ........... 250/231.13, 239, 221, 231.1, 231.14, 250/231.15, 237 R, 237 G; 33/1 N, 1 PT, 33/1 L; 341/11, 13, 14; 356/615, 616, 356/620, 621, 622
See application file for complete search history.

(56) References Cited

U.S. PATENT DOCUMENTS

| | | | | |
|---|---|---|---|---|
| 3,728,551 A | * | 4/1973 | Culver | B23Q 17/22 250/231.16 |
| 3,997,782 A | * | 12/1976 | Willits | G01D 5/3473 250/231.14 |
| 4,317,032 A | * | 2/1982 | Hanus | D05B 69/24 250/231.14 |
| 4,446,715 A | | 5/1984 | Bailey | |
| 4,960,128 A | | 10/1990 | Gordon et al. | |
| 4,964,408 A | | 10/1990 | Hink et al. | |
| 5,041,187 A | | 8/1991 | Hink et al. | |
| 5,065,012 A | * | 11/1991 | Moriyama | G01D 5/34715 250/231.14 |
| 5,069,213 A | | 12/1991 | Polczynski | |
| 5,107,844 A | * | 4/1992 | Kami | A61B 8/12 600/446 |

(Continued)

OTHER PUBLICATIONS

US 8,845,543, 09/2014, Diab et al. (withdrawn)

*Primary Examiner* — Que T Le
*Assistant Examiner* — Jennifer Bennett
(74) *Attorney, Agent, or Firm* — Knobbe, Martens, Olson & Bear, LLP

(57) ABSTRACT

A double-bearing position encoder has an axle stabilized within a housing via two bearings disposed on opposite walls of the housing. The axle is in communications with a rotating cam. The cam actuates a pulser so as to generate an active pulse at a tissue site for analysis by an optical sensor. The axle rotates a slotted encoder wheel or a reflective encoder cylinder disposed within the housing so as to accurately determine the axle position and, hence, the active pulse frequency and phase.

13 Claims, 23 Drawing Sheets

(56) References Cited

U.S. PATENT DOCUMENTS

| | | |
|---|---|---|
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,104,023 A * | 8/2000 | Maeda ............... G01D 5/34 250/231.13 |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |

(56) References Cited

U.S. PATENT DOCUMENTS

| | | |
|---|---|---|
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |

(56) References Cited

U.S. PATENT DOCUMENTS

| | | |
|---|---|---|
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |

(56) References Cited

U.S. PATENT DOCUMENTS

| | | |
|---|---|---|
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |

(56) References Cited

U.S. PATENT DOCUMENTS

| | | |
|---|---|---|
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0371548 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |

\* cited by examiner

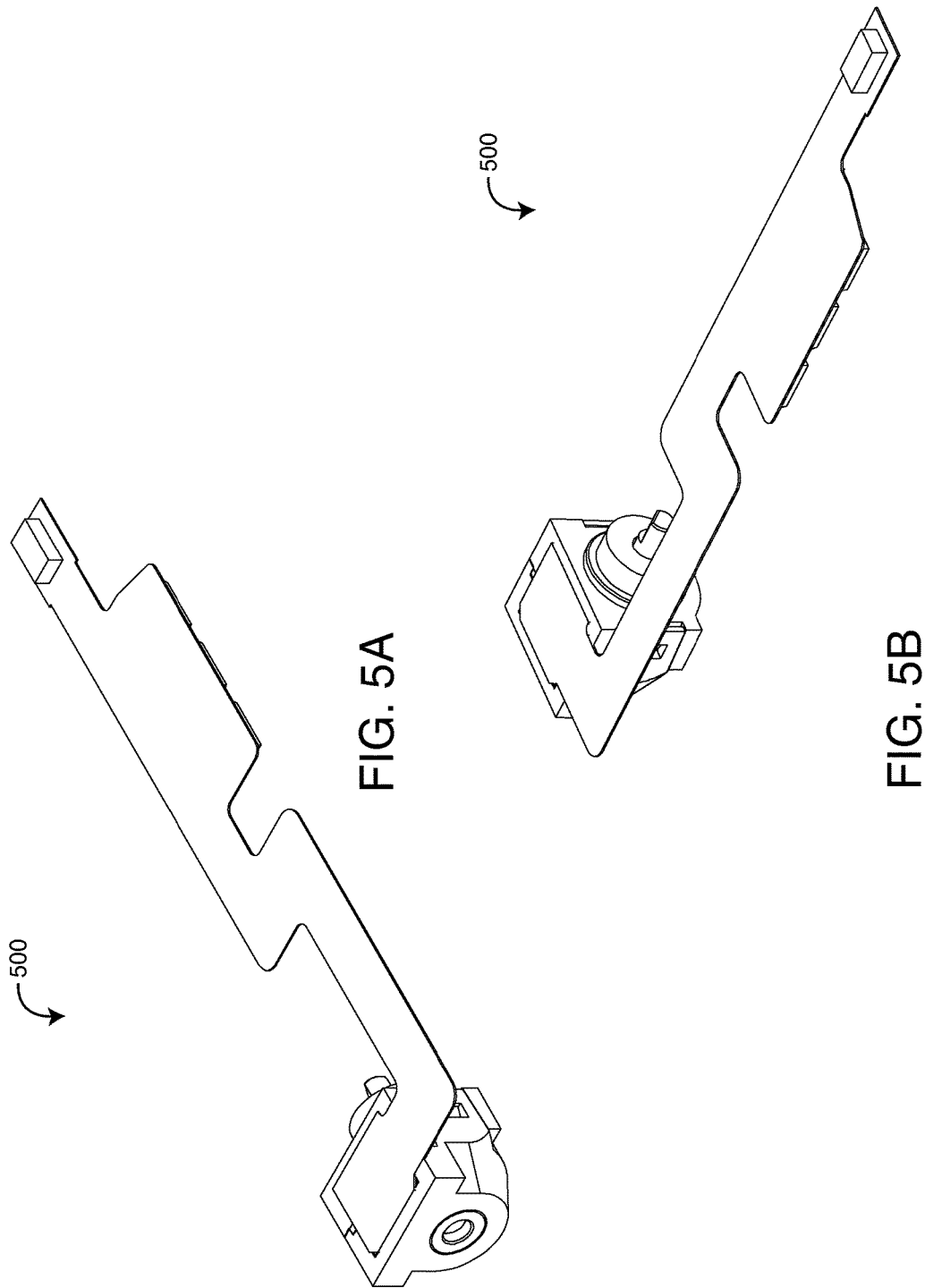

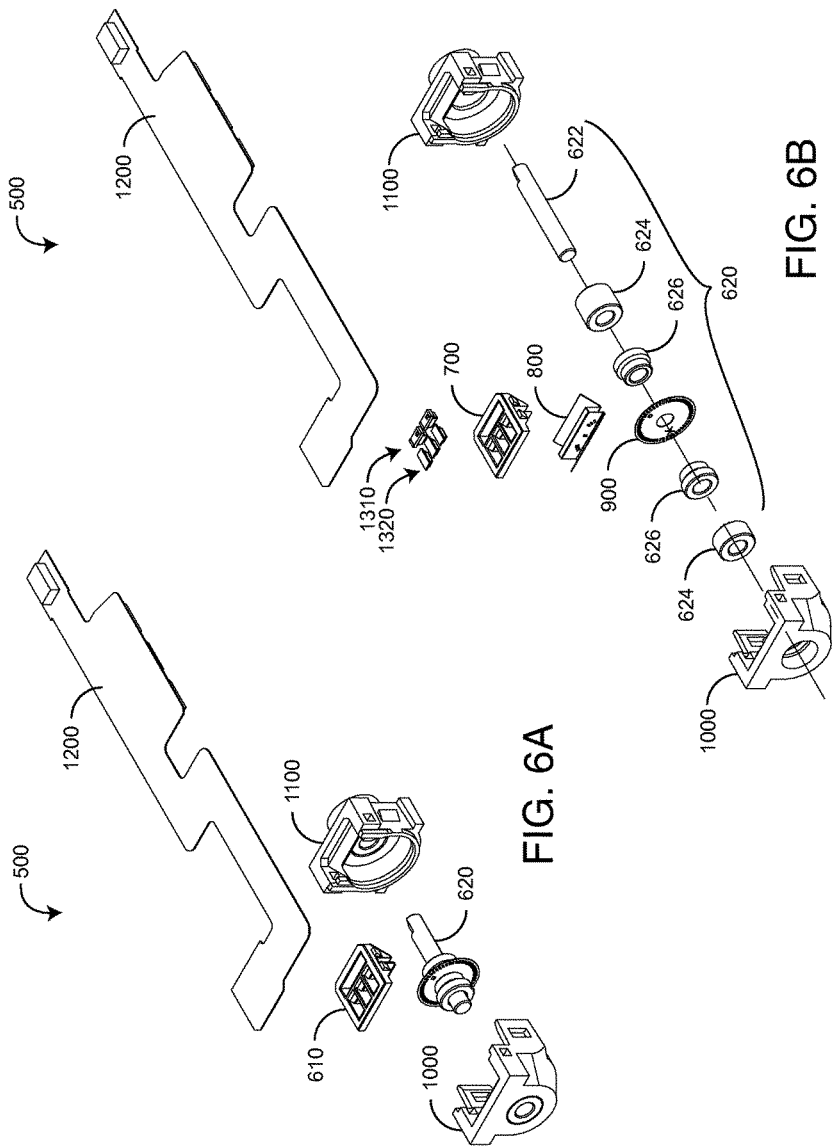

FIG. 9B
FIG. 9D
FIG. 9A
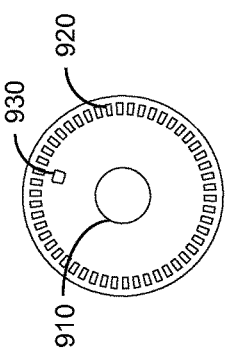
FIG. 9C

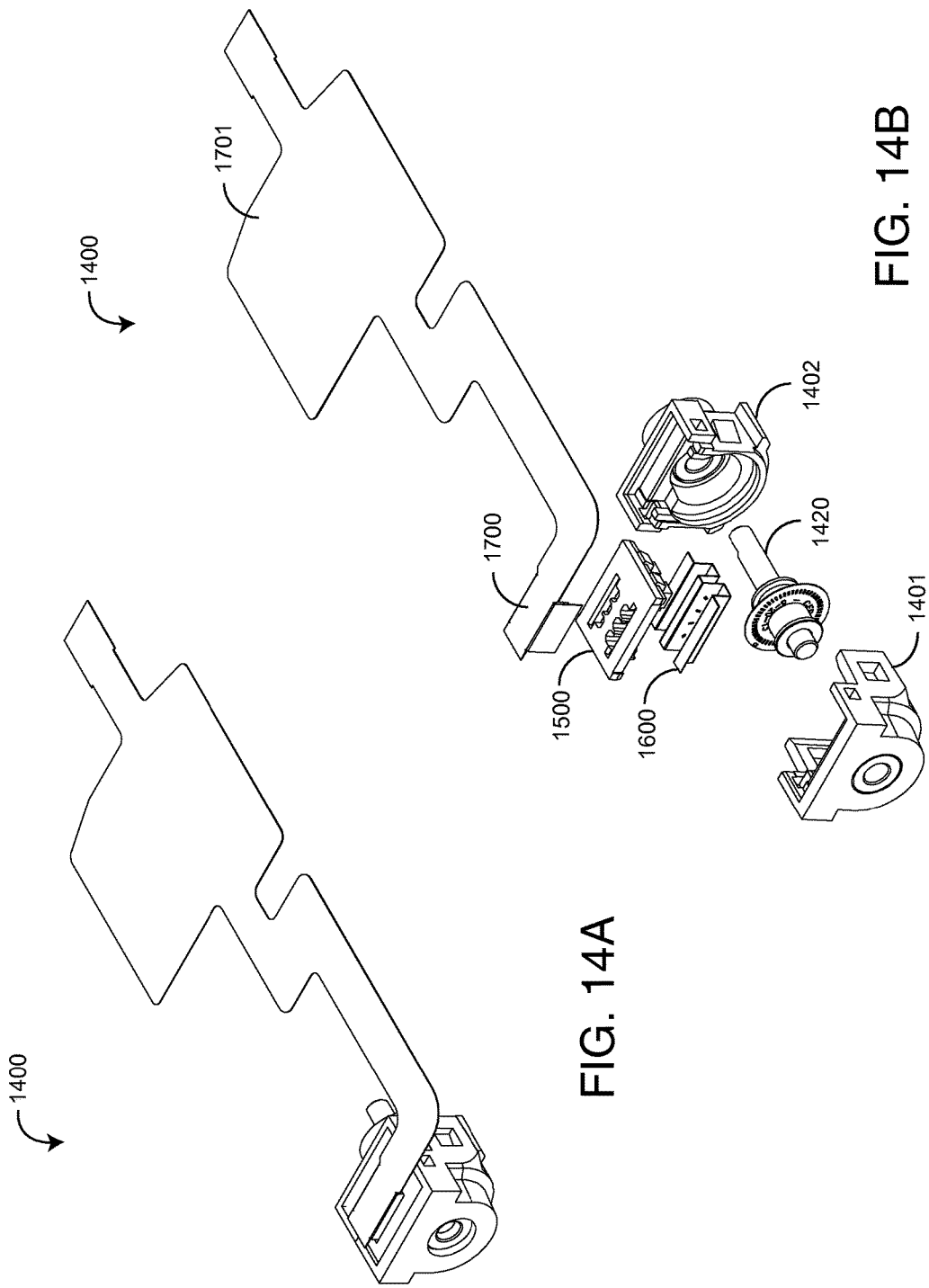

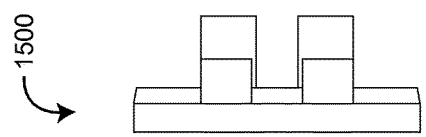
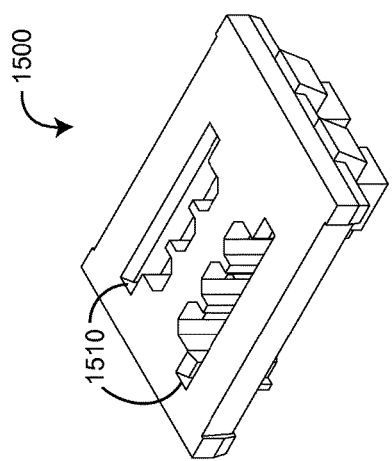
FIG. 15B
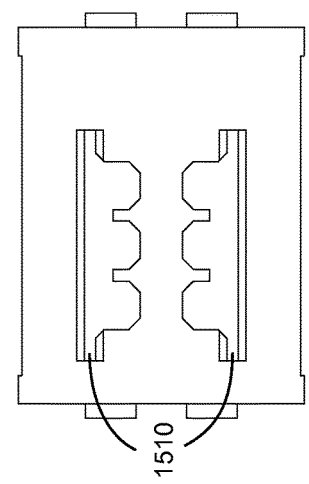
FIG. 15D
FIG. 15A
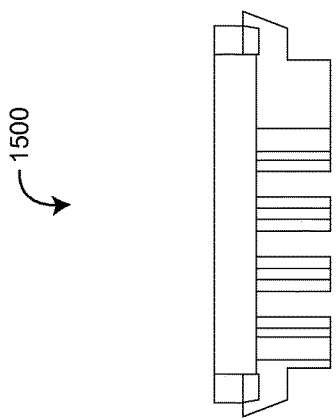
FIG. 15C

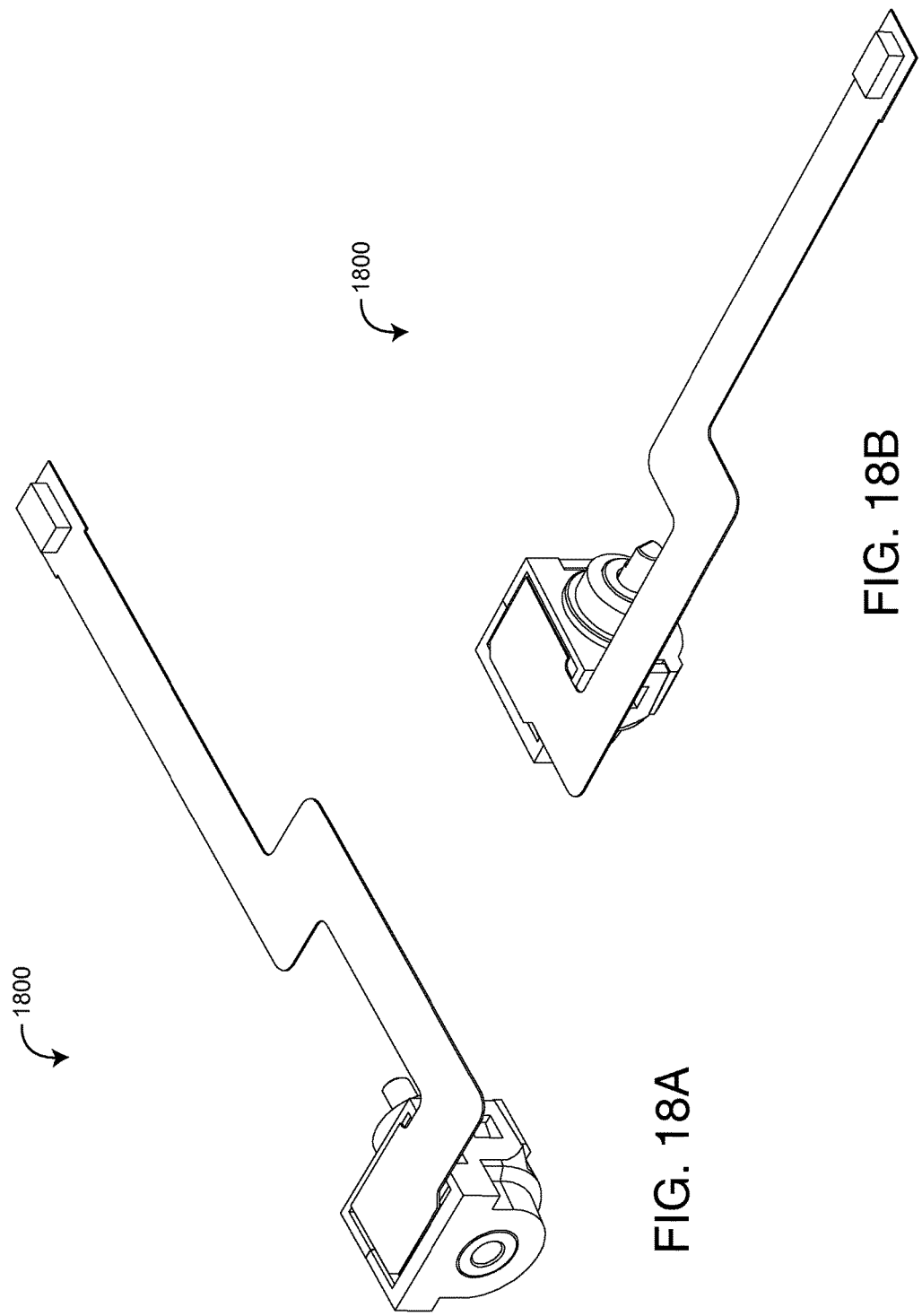

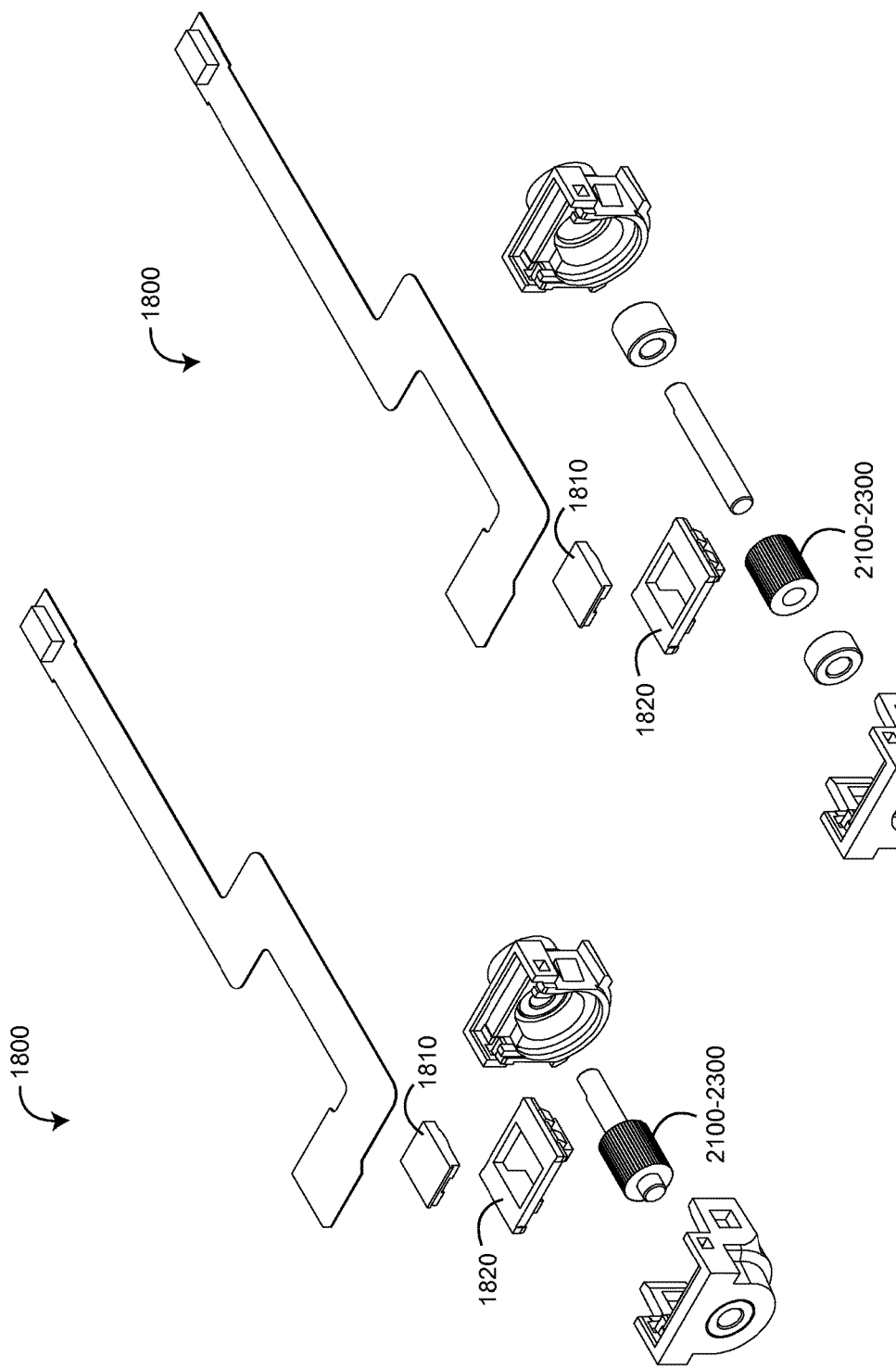

PULSER WITH DOUBLE-BEARING POSITION ENCODER FOR NON-INVASIVE PHYSIOLOGICAL MONITORING

PRIORITY CLAIM AND REFERENCE TO RELATED APPLICATIONS

The present application claims priority benefit under 35 U.S.C. § 119(e) to U.S. Provisional Patent Application Ser. No. 61/847,307, filed Jul. 17, 2013 titled Double-Bearing Position Encoder, which is hereby incorporated in its entirety by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a photoplethysmograph signal responsive to the emitted light after attenuation by pulsatile blood flow within the tissue site. The cable transmits the detector signal to the monitor, which processes the signal to provide a numerical readout of oxygen saturation ($SpO_2$) and pulse rate, along with an audible pulse indication of the person's pulse. The photoplethysmograph waveform may also be displayed.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entireties by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entireties by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled *Multiple Wavelength Sensor Equalization*; U.S. Pat. No. 7,729,733, filed Mar. 1, 2006, titled *Configurable Physiological Measurement System*; U.S. Pat. Pub. No. 2006/0211925, filed Mar. 1, 2006, titled *Physiological Parameter Confidence Measure* and U.S. Pat. Pub. No. 2006/0238358, filed Mar. 1, 2006, titled *Noninvasive Multi-Parameter Patient Monitor*, all assigned to Cercacor Laboratories, Inc., Irvine, Calif. ("Cercacor") and all incorporated in their entireties by reference herein. An advanced parameter measurement system that includes acoustic monitoring is described in U.S. Pat. Pub. No. 2010/0274099, filed Dec. 21, 2009, titled *Acoustic Sensor Assembly*, assigned to Masimo and incorporated in its entirety by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios.

FIG. 1 illustrates an active pulse generator 100 that installs within a reusable optical sensor for precisely pulsing a tissue site, such a fingertip. The active pulse generator 100 has a motor 110, a cam 120, a housing 130, a pulser 140 and an optical encoder 200. The cam 120 and pulser 140 are located within the housing 130. A shaft 160 couples the motor 110 to the cam 120 so as to linearly-actuate the pulser 140 upon application of electric current to the motor 110. The encoder 200 extends into the housing 130 so as to mechanically couple to the cam 120. The encoder 200 measures the rotation of the cam 120 and hence the position of the pulser 140. Based upon encoder feedback, the pulser 140 frequency and phase, and hence that of an active pulse, can be accurately measured and controlled. An active pulse reusable optical sensor is described in U.S. patent application Ser. No. 13/473,477, titled *Personal Health Device*, filed May 16, 2012 and assigned to Cercacor is hereby incorporated in its entirety by reference herein.

FIG. 2 further illustrates the encoder 200, which has a housing 210, a single-bearing 220 that mounts an encoder axle 230 to an encoder wheel 240 and an optics assembly that senses reflective position tracks and an index track on the encoder wheel 240 so as to generate a two-channel quadrature square wave output indicative of the axle 230 position.

SUMMARY OF THE INVENTION

A single-bearing encoder wheel mount, as described with respect to FIG. 2, above, has insufficient mechanical stability to provide optimum accuracy in measuring and controlling the phase and frequency of an optical sensor active pulse. Double-bearing position encoder embodiments advantageously improve encoder wheel stability so as to improve active pulse accuracy and also solve encoder wheel/optical reader configuration issues created by the necessary location of the stabilizing second bearing.

One aspect of a double-bearing position encoder is a housing, a pair of bearings disposed within opposite facing walls of the housing and an axle disposed within the housing and supported by the bearings. The axle is in mechanical communications with a pulser. An encoder wheel having wheel slots is fixedly attached to the axle. An LED is disposed within the housing so as to illuminate the encoder wheel. A detector is responsive to the LED illumination after optical interaction with the wheel slots as the axle rotates the wheel so as to indicate the wheel position.

In an embodiment, the axle is stabilized within a housing via bearings disposed on opposite walls of the housing. The axle is in communications with a rotating cam that actuates a pulser so as to generate an active pulse at a tissue site for analysis by an optical sensor. The axle rotates a slotted encoder wheel or a reflective encoder cylinder so as to accurately determine the axle position and, hence, the active pulse frequency and phase.

In various embodiment, the encoder comprisies an encoder mask having mask slots disposed over an edge and along both sides of the encoder wheel so that the LED illumination passes through the mask slots and the wheel slots before reaching the detector. The encoder mask is folded so that LED light is reflected off of the mask a first time before illuminating the encoder wheel and second time before reaching the detector. Alternatively, the encoder mask is folded so that LED light is not reflected off of the mask before illuminating the encoder wheel and before reaching the detector.

Another aspect of a double-bearing position encoder is a rotatable axle. An encoder wheel is rotatably mounted on the double-bearing-mounted axle. An encoder mask is folded proximate an outer edge of the encoder wheel. Wheel slots are disposed around the encoder wheel proximate the outer edge. Mask slots are disposed through the encoder mask, and an emitter and a detector are disposed proximate to and on either side of the encoder wheel so that light intermittently passes through the encoder wheel via the wheel slots and the mask slots.

In various embodiments, light is reflected from the emitter off of the mask at least once before it reaches the detector. Light is reflected from the emitter off of the mask twice before it reaches the detector. The emitter directly illuminates the detector without reflection off the mask.

A further aspect of a double-bearing position encoder is a double bearing means of stabilizing a rotatable axle within an encoder housing. An encoder wheel means fixedly mounted to the axle so as to rotate as the axle rotates. An illumination and detection means of intermittently passing light through the encoder wheel means as it rotates, and a folded and slotted mask means of precisely passing light through encoder wheel.

BRIEF DESCRIPTION OF THE DRAWINGS

FIGS. 5A-B are front and back perspective views of a double-bearing position encoder assembly;

FIGS. 6A-B are partially exploded and exploded perspective views, respectively, of a double-bearing position encoder assembly;

FIGS. 9A-D are top, perspective, front and side views, respectively, of a slotted encoder wheel;

FIGS. 14A-B are assembled and partially exploded perspective views, respectively, of another double-bearing position encoder assembly;

FIGS. 15A-D are front, perspective, top and side views, respectively, of an encoder mask block;

FIGS. 18A-B are front and back perspective views of a further double-bearing position encoder assembly;

FIGS. 20A-B are top mostly exploded and exploded perspective views, respectively, of a further double-bearing position encoder assembly;

DETAILED DESCRIPTION OF THE PREFERRED EMBODIMENTS

Generally

Figure 1:
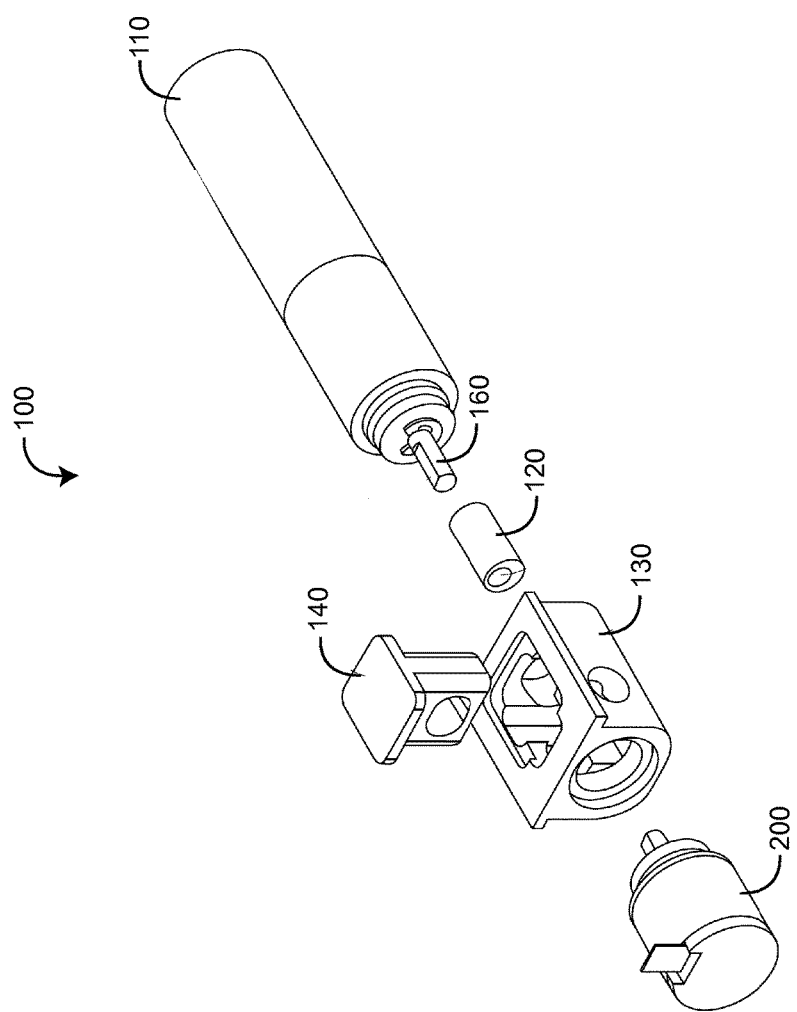
FIG. 1 is a perspective illustration of an optical sensor active pulse generator including a single-bearing position encoder.
Figure 2:
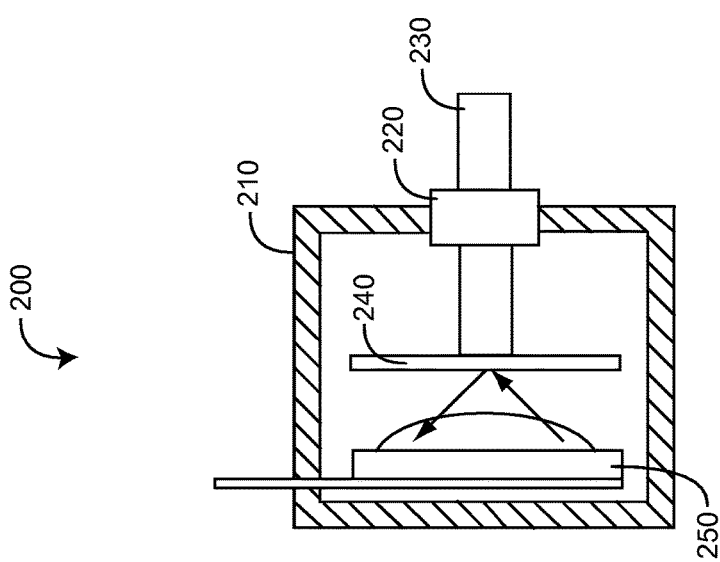
FIG. 2 is a cutaway side view of a single-bearing position encoder.

FIGS. 3-23 illustrate three position-encoder embodiments. Each of these embodiments advantageously utilize a double-bearing axle to stably mount an optical encoding device for the most precise optical measurements of the axle angular position and, hence, the linear position versus time of a pulser 140 (FIG. 1). In this manner, a precisely measured and controlled sensor active pulse can be generated.

Figures 3A, 3B:
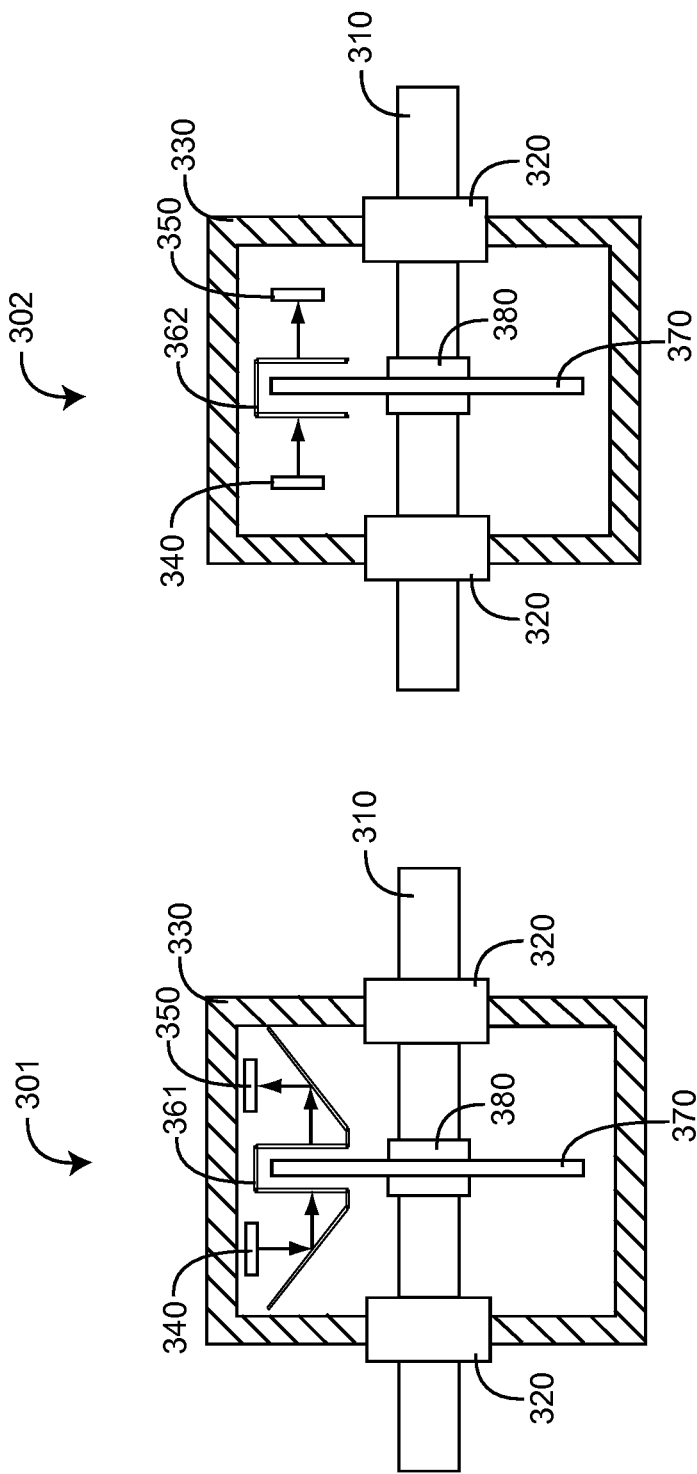
FIGS. 3A-B are cutaway side views of double-bearing position encoder embodiments incorporating a slotted wheel encoder.

FIGS. 3A-B generally illustrate slotted-wheel, position-encoder 301, 302 embodiments. The encoders 301, 302 each have an axle 310 with a double-bearing 320 mount to a housing 330. The slotted wheel 370 is mounted to the axle 310. LEDs 340 illuminate a wheel obverse side and detectors 350 sense the illumination through wheel slots on a wheel reverse side. A folded, slotted mask 361 is positioned on both sides of the slotted wheel 370 so that mask slots align with wheel slots at discrete axle positions. Accordingly, axle position pulses are generated as the axle 310 rotates the wheel 340 and the wheel slots alternately block and pass light, as generated and sensed with the LED/detector optics 340, 350.

As shown in FIG. 3A, the LED/detector optics 340, 350 are located perpendicular to the slotted wheel, and the mask 361 is reflective. A slotted wheel position encoder embodiment according to FIG. 3A is described in detail with respect to FIGS. 5-13, below.

As shown in FIG. 3B, the LED/detector optics 340, 350 are located parallel to the slotted wheel so as to directly illuminate and sense via the mask 362. A slotted wheel position encoder embodiment according to FIG. 3B is described in detail with respect to FIGS. 14-17, below.

Figure 4:
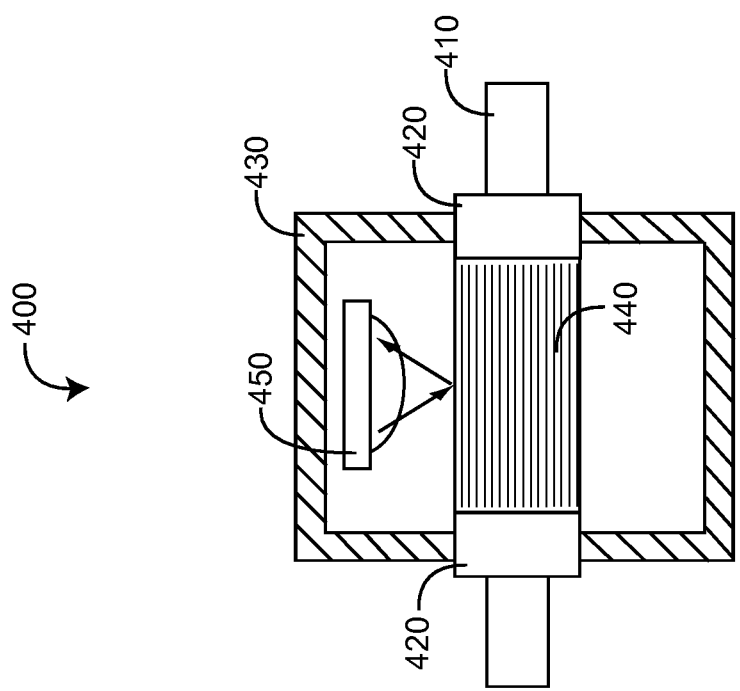
FIG. 4 is a cutaway side view of a double-bearing position encoder embodiment incorporating a reflective cylinder encoder.
Figure 7E:
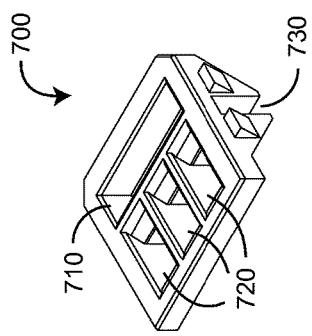
FIGS. 7A-E are top, front, bottom, side and perspective views, respectively, of an encoder mask block.
Figure 7D:
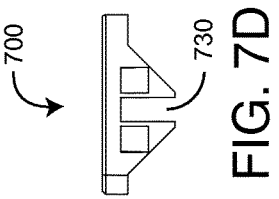
Figure 7A:
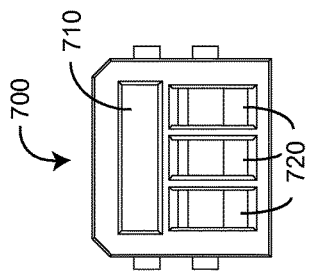
Figure 7B:
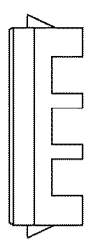
Figure 7C:
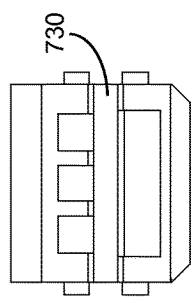
Figure 8B:
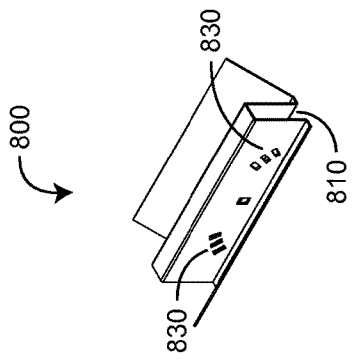
FIGS. 8A-D are top, perspective, front and side views, respectively, of an encoder mask.
Figure 8D:
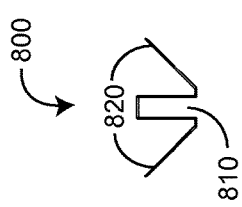
Figure 8A:
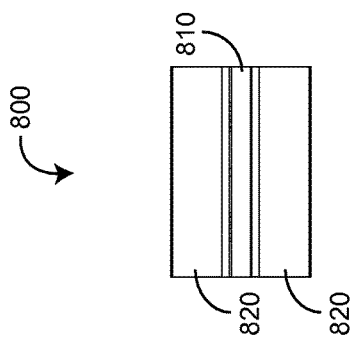
Figure 8C:
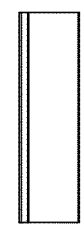
Figure 10B:
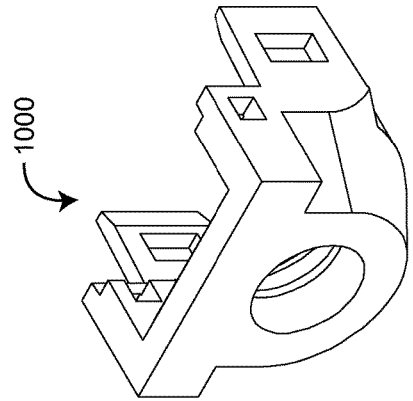
FIGS. 10A-E are top, perspective, front, back and side views, respectively, of an encoder front housing.
Figure 10E:
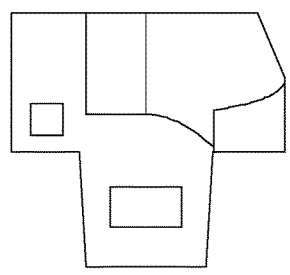
Figure 10D:
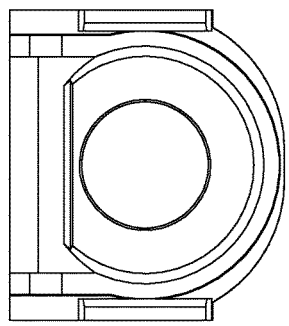
Figure 10A:
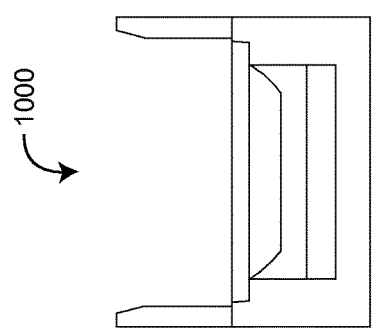
Figure 10C:
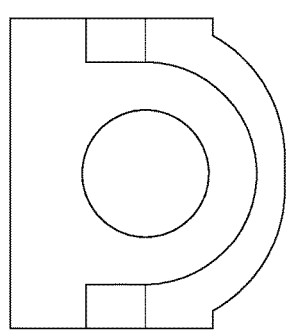
Figure 11B:
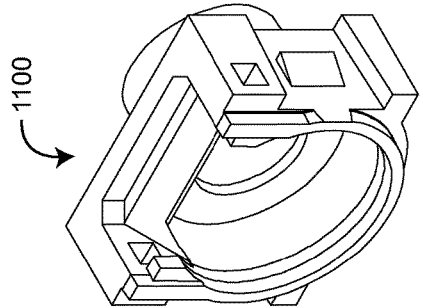
FIGS. 11A-E are top, perspective, front, back and side views, respectively, of an encoder back housing.
Figure 11E:
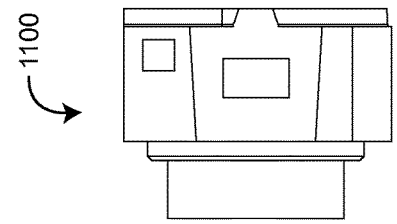
Figure 11D:
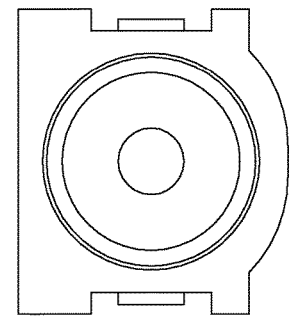
Figure 11A:
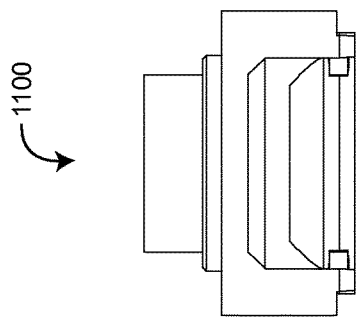
Figure 11C:
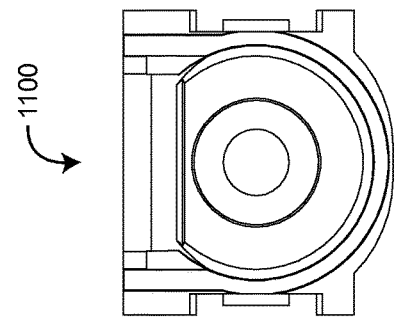
Figure 12A:
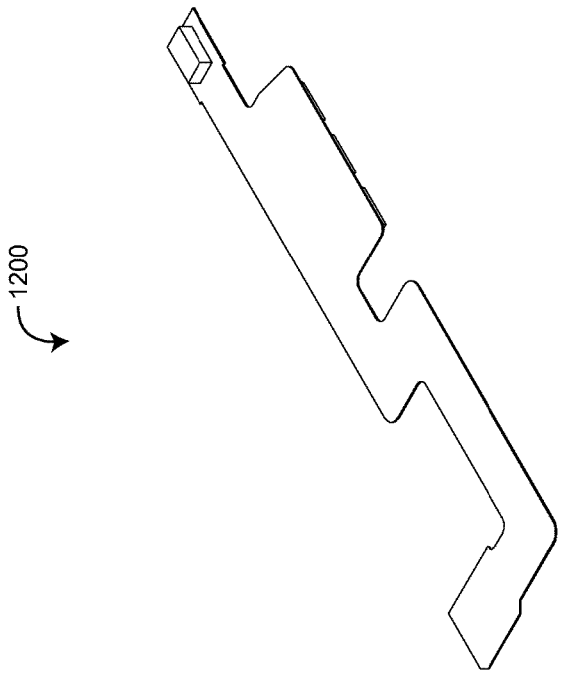
FIGS. 12A-E are top, bottom, perspective, front and side views, respectively, of an encoder flex circuit.
Figure 12B:
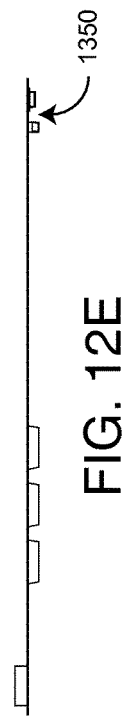
Figure 12C:
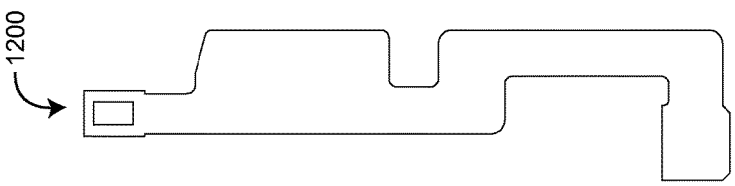
Figure 12D:
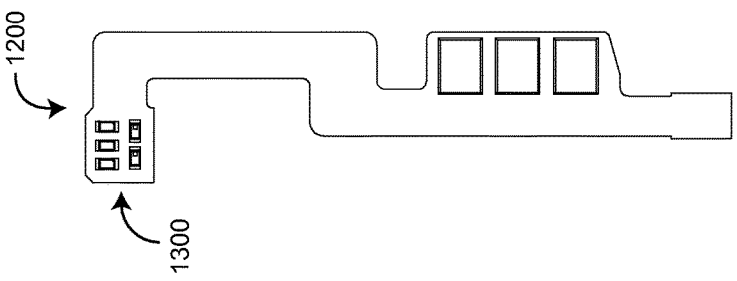
Figure 12E:
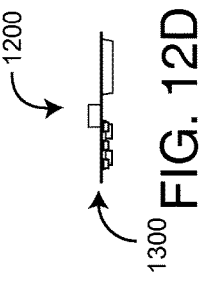

FIG. 4 generally illustrates a reflective-cylinder, position-encoder 400 embodiment. The encoder 400 has an axle 410 with a double-bearing 420 mount to a housing 430. A reflective cylinder 440 is mounted to the axle 410. The cylinder surface has a repetitive reflective structure disposed across the length of the cylinder. A commercial optical encoder 450 is located over the cylinder so as to sense the reflective structure 440 and determine axle position accordingly. In an embodiment, the optical encoder is a 3-channel reflective incremental encoder available from Avago Technologies, San Jose, Calif. A reflective cylinder position encoder embodiment according to FIG. 4 is described in detail with respect to FIGS. 18-23, below.

Slotted Wheel Encoder—Indirect Illumination Encoder Mask

FIGS. 5-13 illustrate details of a double-bearing, slotted-wheel, position-encoder embodiment utilizing an indirectly-illuminated (indirect) encoder mask. FIGS. 5-6 illustrate the double-bearing position encoder 500 assembly which reads an encoder wheel 900 via a wheel-edge-mounted photo interrupter 610. The encoder wheel 900 is part of an encoder assembly 620. The encoder assembly 620 is advantageously mounted within an double-bearing encoder housing 1000, 1100. The photo interrupter 610 includes an encoder mask block 700 that houses a reflective encoder mask (origami) 800, LEDs 1310 and detectors 1320. The LEDs 1310 and detectors 1320 are mechanically mounted to, and in electrical communications with, a flex circuit 1200 that generates LED 1310 drive signals and receives and processes detector 1320 signals. The encoder assembly 620 has a encoder wheel 900 mounted between encoder wheel bushings 626 and shaft bushings 624. The photo interrupter 610 is mounted onto the encoder housing 1000, 1100 over an encoder wheel 900 edge.

Figure 13B:
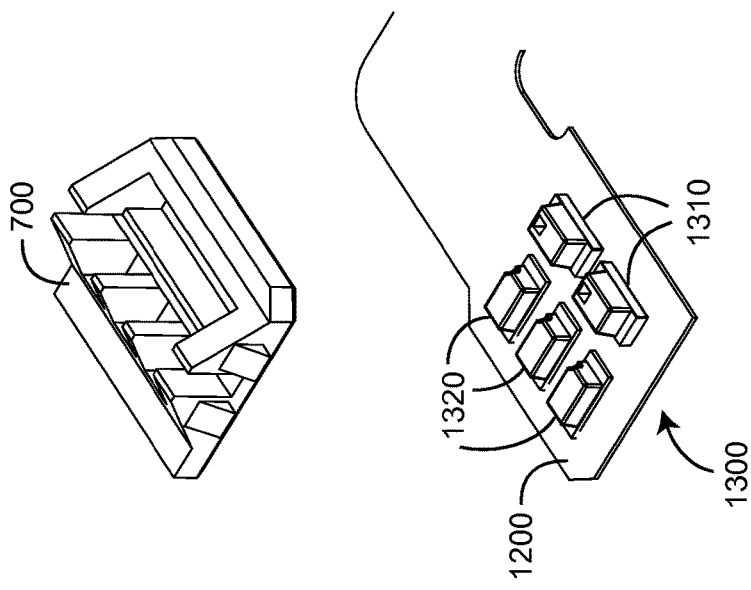
FIGS. 13A-B are top and bottom exploded views, respectively, of flex circuit optics and a corresponding encoder mask block.
Figure 13A:
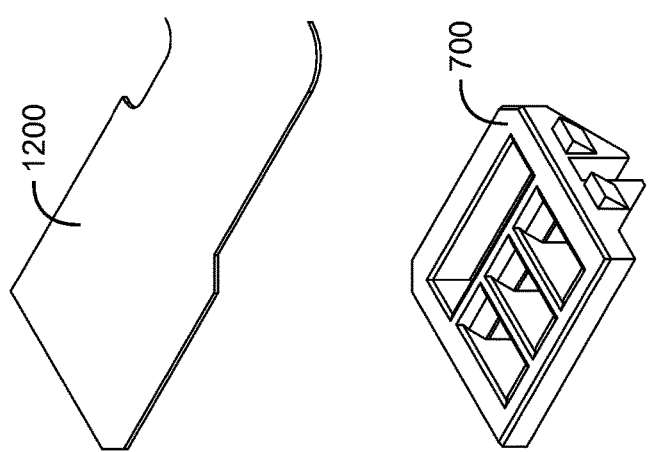
Figure 16A:
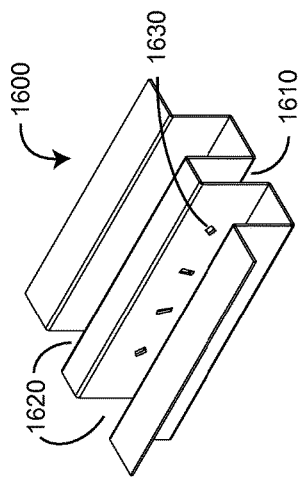
FIGS. 16A-D are front, perspective, top and side views, respectively, of an encoder mask.
Figure 16B:
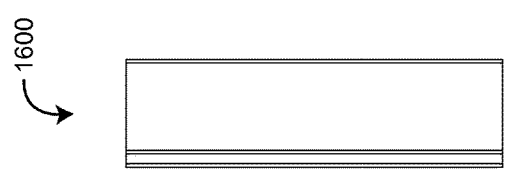
Figure 16C:
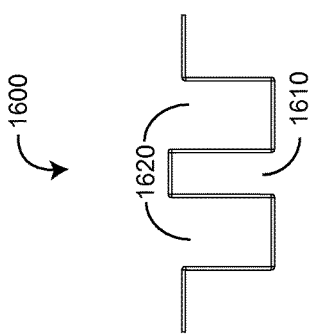
Figure 16D:
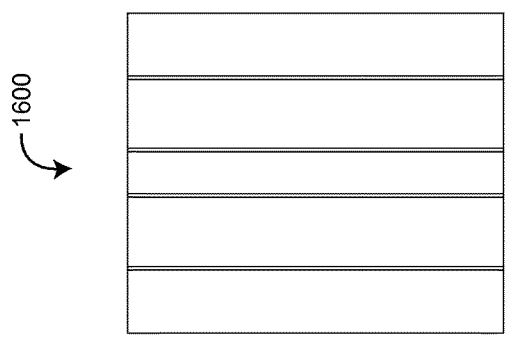

FIGS. 7A-E illustrate an encoder mask block 700 that houses the flex circuit-mounted optics 1310, 1320 (FIGS. 13A-B) proximate to the encoder mask 800 (FIGS. 8A-D). FIGS. 8A-D illustrate the encoder mask 800, which defines an encoder wheel path 810, reflective surfaces 820 and mask slots 830. The encoder mask allows the LEDs/detectors 1310, 1320 (FIG. 13B) to read the wheel slots at 0 and 90 electrical degrees. In particular, LED 1310 (FIG. 13B) light is reflected off one surface 820 through the slots 830 and intermittently through the encoder slots 920 as the encoder 900 spins within the wheel path 810. The intermittent light is reflected off another surface 820 to the detectors 1320 (FIG. 13B). FIGS. 9A-D illustrate a slotted encoder wheel 900 constructed as a thin, round disk defining a center-mount hole 910, encoder slots 920 and an index slot 930.

FIGS. 10-11 illustrate the encoder front housing 1000 and back housing 1100 that advantageously provides a double-bear mount for the encoder assembly 620 (FIGS. 6A-B). Further the housing 1000, 1100 positions the photo interrupter 610 (FIGS. 6A-B) over the encoder wheel 900 so as to detect the passing encoder slots 920 (FIGS. 9A-D). FIGS. 12-13 illustrate the encoder flex circuit assembly 1200 and corresponding optics 1300 and mask block 700, which generate signals responsive to the encoder 900 (FIGS. 9A-D) position as it rotates in response to a shaft-coupled, motor-driven active pulser 110, 120, 140 (FIG. 1).

Slotted Wheel Encoder—Direct Illumination Mask

FIGS. 14-17 illustrate details of a double-bearing, slotted-wheel, position-encoder 1400 embodiment utilizing a direct illumination encoder mask. FIGS. 15A-D illustrate an encoder mask block 1500 that positions flex circuit-mounted optics to the mask 1600 (FIGS. 16A-D). FIGS. 16A-D illustrate the encoder mask origami 1600 having mask slots for reading the wheel slots at 0 and 90 electrical degrees. FIGS. 17A-B illustrate flex circuit optics 1700 and the corresponding encoder mask block 1500 (FIGS. 15A-D).

Figure 17B:
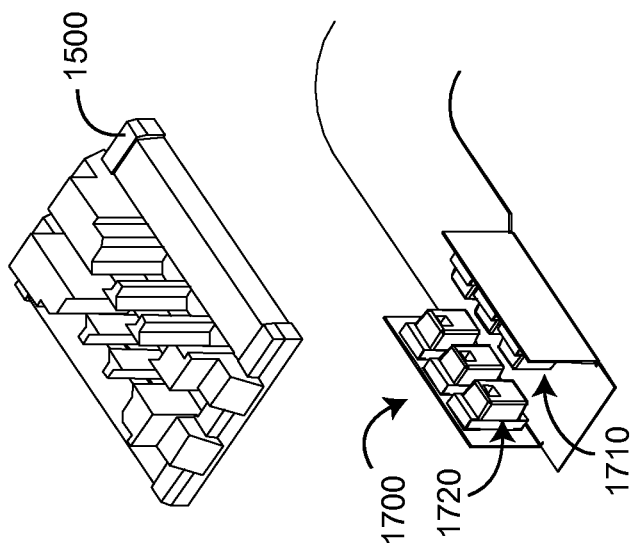
FIGS. 17A-B are top and bottom exploded views, respectively, of flex circuit optics and a corresponding encoder mask block.
Figure 17A:
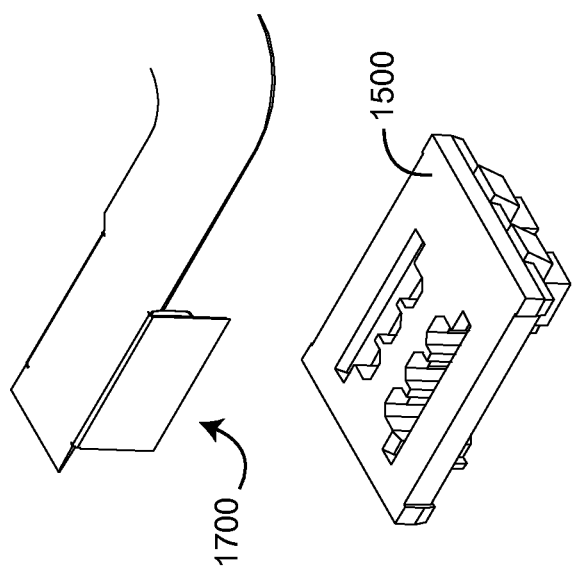

As shown in FIGS. 14A-B, a double-bearing position encoder 1400 assembly reads an encoder wheel portion of an encoder assembly 1420 via a wheel-edge-mounted direct illumination mask 1600 and proximate-mounted LED/detector optics 1700 (FIGS. 17A-B). The encoder assembly 1420 is advantageously mounted within an double-bearing encoder housing 1401, 1402. A photo interrupter includes an encoder mask block 1500 that houses a direct illumination encoder mask 1600, LEDs 1710 (FIG. 17B) and detectors 1720 (FIG. 17B). The LEDs and detectors are mechanically mounted to, and in electrical communications with, a flex circuit 1701 that generates LED drive signals and receives and processes detector signals. The encoder assembly 1420 has a encoder wheel mounted between encoder wheel bushings and shaft bushings as described above. The photo interrupter 1500, 1600 is mounted onto the encoder housing 1401, 1402 over an encoder wheel edge.

FIGS. 15A-D illustrate an encoder mask block 1500 that houses the flex circuit-mounted optics 1710, 1720 (FIGS. 17B) proximate to the encoder mask 1600 (FIGS. 16A-D). FIGS. 16A-D illustrate the encoder mask 1600, which defines an encoder wheel path 1610, a direct optical path 1620 and mask slots 1630. The encoder mask allows the LEDs/detectors 1710, 1720 (FIG. 17B) to read the wheel slots at 0 and 90 electrical degrees. In particular, LED 1710 (FIG. 13B) light is directly transmitted 1620 through the slots 1630 and intermittently through the encoder slots 920 (FIG. 9B) as the encoder spins within the wheel path 1610. The intermittent light is directly transmitted 1620 to the detectors 1720 (FIG. 17B).

Reflective Cylinder Encoder

Figures 19A, 19B:
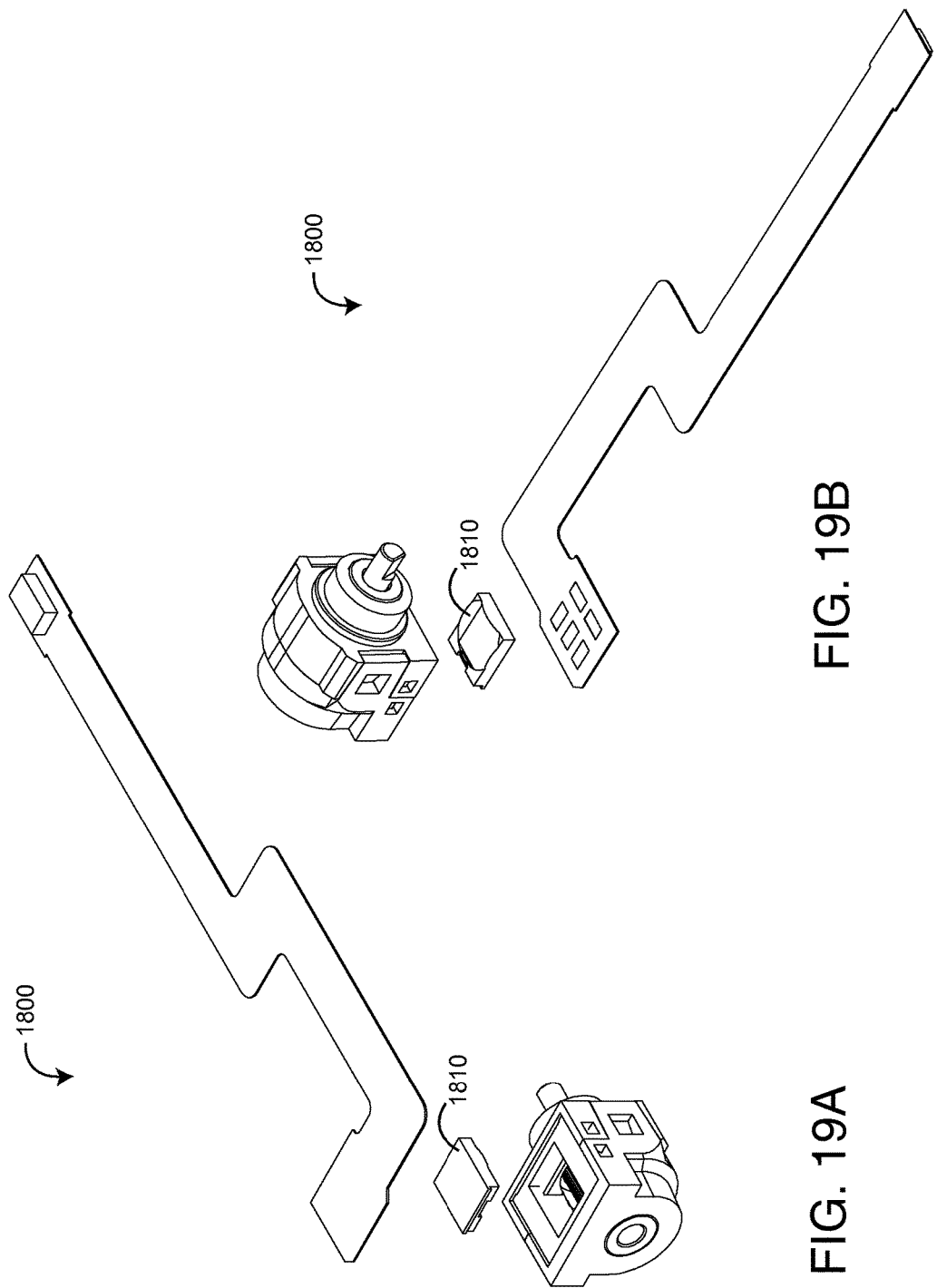
FIGS. 19A-B are top and bottom partially exploded perspective views, respectively, of a further double-bearing position encoder assembly.
Figure 21B:
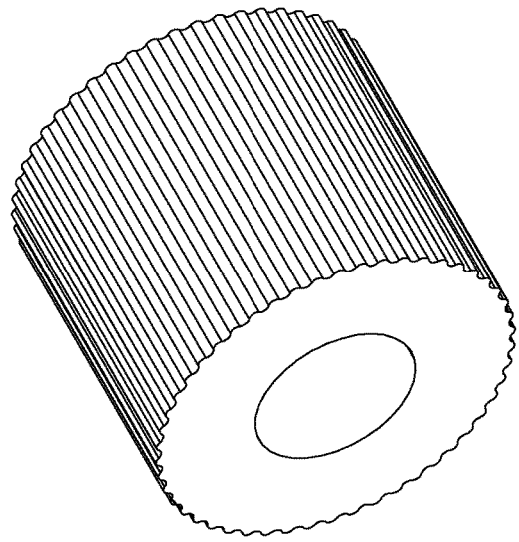
FIGS. 21A-B are front and perspective views, respectively, of a first encoder cylinder embodiment.
Figure 21A:
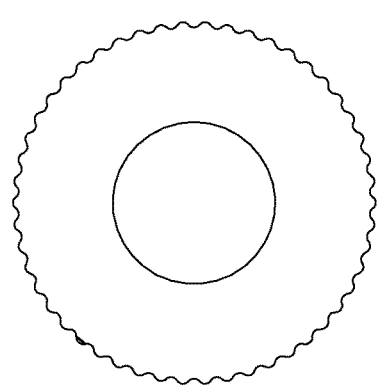
Figure 22B:
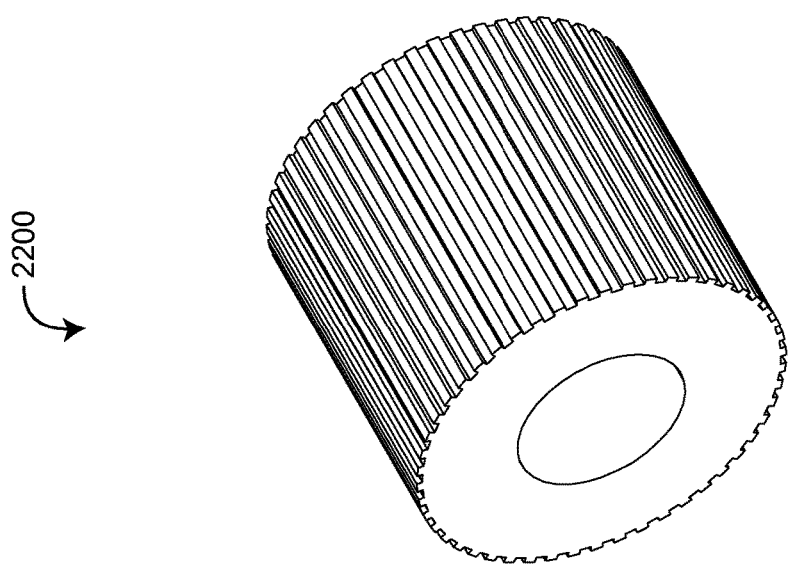
FIGS. 22A-B are front and perspective views, respectively, of a second encoder cylinder embodiment.
Figure 22A:
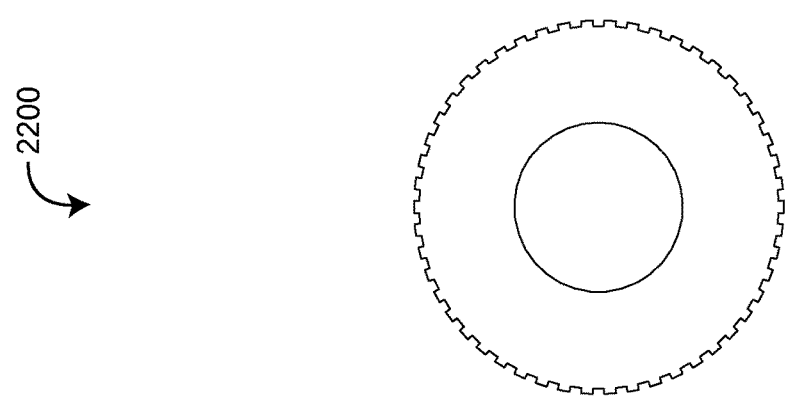
Figure 23B:
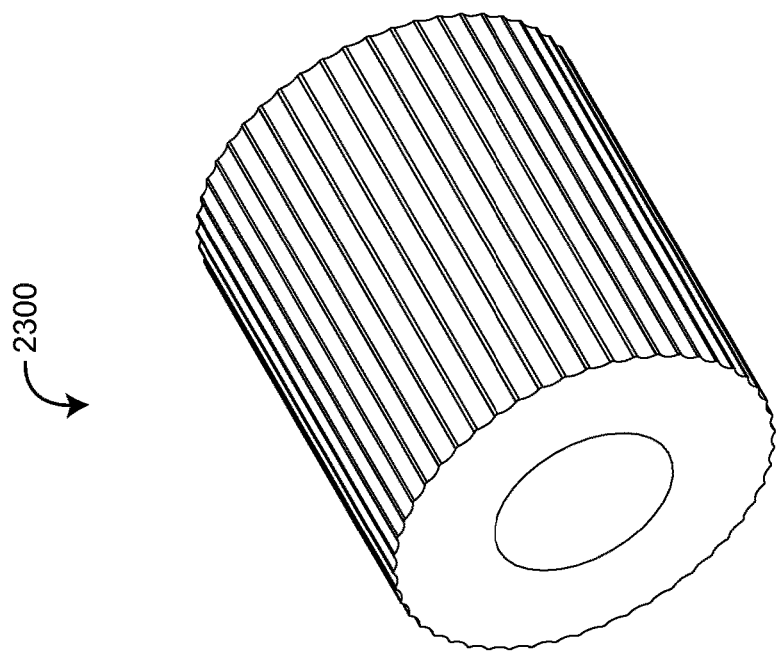
FIGS. 23A-B are front and perspective views, respectively, of a third encoder cylinder embodiment.
Figure 23A:
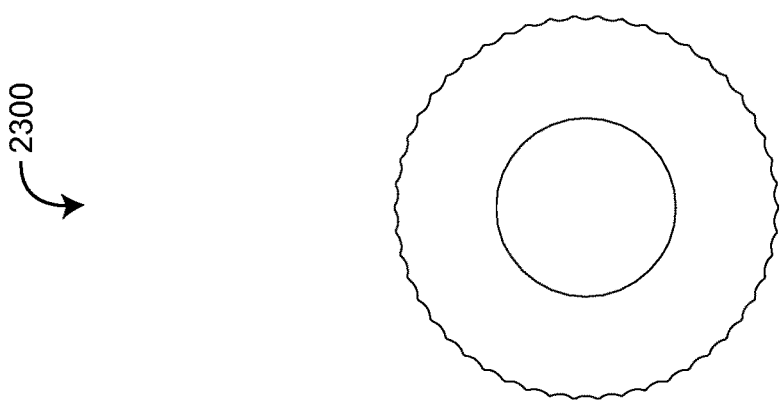

FIG. 18-23 illustrate details of double-bearing, reflective cylinder, position-encoder 1800 embodiment utilizing an off-the-shelf reflective encoder 1810 mounted proximate a double-bearing reflective encoder cylinder 2100-2300 (FIGS. 21-23). FIGS. 18-20 illustrate the double-bearing position encoder 1800 embodiment having an off-the-shelf reflective encoder 1810, an encoder block 1820 and a reflective encoder cylinder 2100-2300. FIGS. 21-23 illustrate various encoder cylinder embodiments.

A double-bearing position encoder has been disclosed in detail in connection with various embodiments. These embodiments are disclosed by way of examples only and are not to limit the scope of the claims that follow. One of ordinary skill in the art will appreciate many variations and modifications.

What is claimed is:

1. A noninvasive optical sensor configured to detect attenuated light from a light source and output a signal responsive to said attenuation, said signal indicative of one or more physiological parameters of a patient, the optical sensor including a double-bearing position encoder including an axle stabilized via bearings disposed within opposite walls, the axle in communications with a rotating cam that actuates a pulser so as to generate an active pulse at a tissue site for analysis by the optical sensor, the axle rotates an encoder so as to accurately determine an axle position and, hence, an active pulse frequency and phase, the optical sensor comprising:

the light source configured to emit light;

one or more photodetectors configured to detect said emitted light after attenuation by tissue of said patient at a measurement site, said one or more photodetectors configured to output said signal responsive to said attenuation, said signal indicative of said one or more physiological parameters of said patient; and the double-bearing position encoder comprising:
a housing,
the bearings disposed within said opposite walls of the housing,
the axle disposed within the housing and supported by the bearings, the axle in mechanical communications with the pulser,
the encoder fixedly attached to the axle and having a plurality of slots,
an LED disposed within the housing that illuminates the encoder;
a detector responsive to the LED illumination after optical interaction with the slots of the encoder as the axle rotates the encoder so as to indicate an encoder position, and
an encoder mask having a plurality of mask slots disposed over an edge and along both sides of the encoder such that light from the LED passes through the mask slots and the slots of the encoder before reaching the detector, wherein the encoder mask is folded such that the light from the LED is reflected off of the mask at least once before reaching the encoder.

2. The noninvasive optical sensor according to claim 1 wherein the encoder mask is configured to reflect the light from the LED off of the mask a first time before passing through the mask slots and the slots of the encoder and a second time before reaching the detector.

3. The noninvasive optical sensor according to claim 1 wherein the mask is configured to reflect the light from the LED off of the mask before passing through the mask slots and the slots of the encoder.

4. The noninvasive optical sensor according to claim 1 wherein the mask is configured to reflect the light from the LED off of the mask after passing through the mask slots and the slots of the encoder.

5. The noninvasive optical sensor according to claim 1 wherein the mask is configured to reflect the light from the LED off of the mask twice before reaching the detector.

6. An encoding method for determining a position of a rotatable axle of a double-bearing position encoder having the axle stabilized via bearings disposed proximate opposing walls, the axle being in communications with a rotating cam that actuates a pulser so as to generate an active periodic perturbation of patient tissue at a tissue site, a noninvasive optical sensor configured to detect attenuated light from a light source and output a signal responsive to said attenuation, said signal indicative of one or more physiological parameters of a patient, the method comprising:
rotatably mounting the encoder on the double-bearing-mounted axle;
folding an encoder mask proximate an edge and along both sides of the encoder;
disposing a plurality of slots through the encoder proximate the edge;
disposing a plurality of mask slots through the encoder mask; and
disposing an emitter and a detector proximate to and on either side of the encoder so that light intermittently passes through the mask slots and through the encoder via the encoder slots, wherein the mask is configured to reflect light from the emitter off of the mask at least once before the light reaches the detector.

7. The encoding method according to claim 6 wherein the mask is further configured to reflect the light from the emitter off of the mask at least twice before the light reaches the detector.

8. The method according to claim 6 wherein the mask is configured to reflect the light from the emitter off of the mask before passing through the mask slots and the slots of the encoder.

9. The method according to claim 6 wherein the mask is configured to reflect the light from the emitter off of the mask after passing through the mask slots and the wheel slots of the encoder.

10. The method according to claim 6 wherein the mask is configured to reflect the light from the emitter off of the mask a first time before passing through the mask slots and the slots of the encoder and second time before reaching the detector.

11. A method of determining an active pulse frequency or phase of a noninvasive optical sensor configured to detect attenuated light from a light source and output a signal responsive to said attenuation, said signal indicative of one or more physiological parameters of a patient, the sensor including a pulser comprising a mechanical element configured to perturb tissue of the patient at a measurement site at a predetermined periodicity, the method comprising:
rotating an axle, said pulser and an encoder being mechanically responsive to said axel, the encoder including a plurality of slots;
emitting light from an LED disposed within a housing of a double-bearing position encoder, wherein the double-bearing position encoder includes the axle, the encoder, an encoder mask, a pair of bearings, and a detector, said light reflecting off of the encoder mask, wherein the encoder mask is disposed over an edge and along both sides of the encoder, and wherein the encoder mask includes a plurality of mask slots configured to intermittently align with the slots of the encoder to permit the passing of the light;
detecting via the detector the light after passage through the mask slots and the slots of the encoder;
electronically determining a position of the encoder based at least in part on the light received by the detector; and
electronically determining at least one of a frequency or phase of the pulser based at least in part on the position of the encoder.

12. The method of claim 11 wherein said emitting light further comprises:
the light from the LED reflecting off of the mask a first time before the light passes through the mask slots and the slots of the encoder; and
the light from the LED reflecting off of the mask a second time a second time before reaching the detector.

13. The method of claim 11 wherein said emitting light further comprises:
the light from the LED reflecting off of the mask twice before the light reaches the detector.

* * * * *